US010292999B2

(12) United States Patent
Mani et al.

(10) Patent No.: US 10,292,999 B2
(45) Date of Patent: May 21, 2019

(54) TREATMENT OF ENTERIC STRESS FROM HEAT AND INFECTION IN HUMANS AND ANIMALS BY SUPPLEMENTATION WITH ZINC AND BUTYRIC ACID (71) Applicant: Kemin Industries, Inc., Des Moines, IA (US)

(72) Inventors: Venkatesh Mani, Ames, IA (US); Jon Rubach, West Des Moines, IA (US); Mitchell Poss, Johnston, IA (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 0 days.

(21) Appl. No.: 15/198,833

(22) Filed: Jun. 30, 2016

(65) Prior Publication Data
US 2017/0027984 A1    Feb. 2, 2017

Related U.S. Application Data (60) Provisional application No. 62/186,831, filed on Jun. 30, 2015.

(51) Int. Cl.
*A61K 33/30* (2006.01)
*A61K 31/19* (2006.01)
*A23K 20/105* (2016.01)
*A23K 20/20* (2016.01)
*A23K 50/20* (2016.01)
*A23K 50/75* (2016.01)
*A23K 50/30* (2016.01)
*A23K 20/158* (2016.01)

(52) U.S. Cl.
CPC .......... *A61K 33/30* (2013.01); *A23K 20/105* (2016.05); *A23K 20/158* (2016.05); *A23K 20/30* (2016.05); *A23K 50/20* (2016.05); *A23K 50/30* (2016.05); *A23K 50/75* (2016.05); *A61K 31/19* (2013.01)

(58) Field of Classification Search
CPC ...... A61K 31/19; A61K 33/30; A23K 20/105; A23K 50/20; A23K 50/75; A23K 50/30; A23L 20/30
See application file for complete search history.

(56) References Cited

U.S. PATENT DOCUMENTS

| 4,759,932 | A | 7/1988 | Laurent et al. | |
| 6,733,759 | B2 * | 5/2004 | Ivey | A61K 39/39 424/184.1 |
| 2007/0259954 | A1 * | 11/2007 | Pablos | A23K 20/30 514/494 |
| 2008/0031998 | A1 * | 2/2008 | Marcussen | A23K 40/20 426/2 |
| 2011/0021461 | A1 * | 1/2011 | Vazquez-Anon | A61K 31/47 514/64 |
| 2011/0311634 | A1 * | 12/2011 | Goethals | A23K 40/30 424/490 |
| 2014/0377373 | A1 | 12/2014 | Mullin et al. | |

FOREIGN PATENT DOCUMENTS

| CN | 1775064 A | 5/2006 | |
| DE | 19941570 | 9/1998 | |
| EP | 0689834 | 1/1996 | |
| WO | WO 93/16708 | * 9/1993 | ............. A61K 33/30 |
| WO | WO 00/48613 | * 8/2000 | ............. A61K 33/30 |
| WO | 0056167 | 9/2000 | |
| WO | WO 2009142755 A2 | * 11/2009 | ........... A61K 31/137 |

OTHER PUBLICATIONS

Edmonds et al., "Effect of supplemental humic and butryric acid on performance and mortality in broilers raised under various environmental conditions", "Journal of Applied Poultry Research", Jan. 1, 2014, vol. 23.
Fernandez et al., "Effects of supplemental zinc amino acid complex on gut integrity in heat-stressed growing pigs", "Animal", Jan. 1, 2014, pp. 43-50, vol. 8, No. 1.
Mani et al., "The protective effects of Butipearl Z during heat stress as measured through in vitro studies with swine intestinal epithelial cells and an in vivo swine trial", "Journal of Animal Science", Apr. 1, 2016, p. 150, vol. 94.
Gupte, "Acute heat treatment improves insulin-stimulated glucose uptake in aged skeletal muscle", "J Appl Physiol", Jan. 1, 2011, pp. 451-457, vol. 110.
Sohail et al., "Alleviation of cyclic heat stress in broilers by dietary supplementation of mannan-oligosaccharide and Lactobacillus-based probiotic: Dynamics of cortisol, thyroid hormones, cholesterol C-reactive protein, and humoral immunity", "Poultry Science Association Inc.", Jan. 1, 2010.
Roselli et al., "Alternatives to in-feed antibiotics in pigs: Evaluation of probiotics, zinc or organic acids as protective agents for the intestinal mucosa. A comparison of in vitro and in vivo results", Jan. 1, 2005, pp. 203-218, vol. 54, Publisher: Anim. Res.
Lu et al., "Butyrate supplementation to gestating sows and piglets induces muscle and adipose tissue oxidative genes and improves growth performance", "J Anim. Sci.", Jan. 1, 2012, pp. 430-432, vol. 90, Publisher: American Society of Animal Science.
Ma et al., "Butyrate promotes the recovering of intestinal wound healing through its positive effect on the tight iunctions", "J Anim. Sci", Jan. 1, 2012, pp. 266-268, vol. 90, Publisher: American Society of Animal Science.
Peng et al., "Butyrate Enhances the Intestinal Barrier by Facilitating Tight Junction Assembly via Activation of AMP-Activated Protein Kinase in Caco-2 Cell Monolayers", "Biochemical, Molecular, and Genetic Mechanisms", Jan. 1, 2009, Publisher: The Journal of Nutrition.

(Continued)

Primary Examiner — Doan T Phan
(74) Attorney, Agent, or Firm — Nyemaster Goode P.C.

(57) ABSTRACT

A method of improving intestinal integrity and reducing the effects of heat stress, enteric disease challenges and other intestinal stress conditions in humans and animals by feeding an efficacious amount of a salt of zinc and butyric acid.

17 Claims, 7 Drawing Sheets

(56) References Cited

OTHER PUBLICATIONS

Russo et al., "Butyrate Attenuates Lipopolysaccharide-Induced Inflammation in Intestinal Cells and Crohns Mucosa through Modulation of Antioxidant Defense Machinery", "Butyrate and Inflammation in Crohns Disease", Mar. 1, 2012, vol. 7, No. 3, Publisher: PLOS.

Miyoshi et al., "Cellular zinc is required for intestinal epithelial barrier maintenance via the regulation of claudin-3 and occludin expression", "regulation of claudin-3 and occludin expression", Jan. 1, 2016.

Pasternak et al., "Claudin-4 Undergoes Age-Dependent Change in Cellular Localization on Pig Jejunal Villous Epithelial Cells, Independent of Bacterial Colonization", "Mediators of Inflammation", Jan. 1, 2015, Publisher: Hindawi Publishing Corporation.

Shen et al., "Coated zinc oxide improves intestinal immunity function and regulates microbiota composition in weaned piglets", "British Journal of Nutrition", Jan. 1, 2014, pp. 2123-2134, vol. 111, Publisher: The Authors.

Wang et al., "Comparative effects of sodium butyrate and flavors on feed intake of lactating sows and growth performance of piglets", "Animal Science Journal", Jan. 1, 2014, pp. 683-689, vol. 85, Publisher: Japanese Society of Animal Science.

Kelly et al., "Crosstalk between Microbiota-Derived Short-Chain Fatty Acids and Intestinal Epithelial HIF Augments Tissue Barrier Function", Jan. 1, 2015, Publisher: Elsevier.

Chauhan et al., "Dietary antioxidants at supranutritional doses improve oxidative status and reduce the negative effects of heat stress in sheep", "J. Anim. Sci.", Jan. 1, 2014, pp. 3364-3374, vol. 92, Publisher: ASAS.

St Pierre et al., "Economic Losses from Heat Stress by US Livestock Industries", "J. Dairy Sci.", Jan. 1, 2003, p. E52E77, vol. 86, Publisher: American Dairy Science Association.

Huang et al., "Effect of dietary zinc supplementation on *Escherichia coli* septicemia in weaned pigs", "Swine Health and Production", Jan. 1, 1999, pp. 109-111, vol. 7, No. 3.

Kluger et al., "Effect of heat stress on LPS induced fever and tumor necrosis factor", "American Journal of Physiology", Jan. 1, 1997, pp. R858-R863, vol. 273, No. 3.

Yu et al., "Effect of heat stress on the porcine small intestine: A morphological and gene expression study", "Comparative Biochemistry and Physiology, Part A", Jan. 1, 2010, pp. 119-128, vol. 156, Publisher: Elsevier.

Liu et al., "Effect of dietary zinc oxide on jejunal morphological and immunological characteristics in weaned piglets", "J. Anim. Sci", Jan. 1, 2014, pp. 5009-5018, vol. 92, Publisher: American Society of Animal Science.

Suganuma et al., "Effect of Heat Stress on Lipopolysaccharide-Induced Vascular Permeability Change in Mice", "The Journal of Pharmacology and Experimental Therapeutics", Jan. 1, 2002, vol. 303, No. 2, Publisher: The American Society for Pharmacology and Experimental Therapeutics.

Wang et al., "Effect of heat stress on endotoxin flux across mesenteric-drained and portal-drained viscera of dairy goat", "Journal of Animal Physiology and Animal Nutrition", Jan. 1, 2011, pp. 468-477, vol. 95, Publisher: Blackwell Verlag GmbH.

Chen et al., "Effects of continuous haemofiltration on serum enzyme concentrations endotoxemia, homeostasis and survival in dogs with severe heat stroke", "Resuscitation", Jan. 1, 2012, pp. 657-662, vol. 83, Publisher: Elsevier.

Lodemann et al., "Effects of zinc on epithelial barrier properties and viability in a human and a porcine intestinal cell culture model", "Toxicology in Vitro", Jan. 1, 2013, pp. 834-843, vol. 27, Publisher: Elsevier.

Shelton et al., "Effects of copper sulfate, tri-basic copper chloride, and zinc oxide on weanling pig performance", "J. Anim. Sci.", Jan. 1, 2011, pp. 2440-2451, vol. 89, Publisher: American Society of Animal Science.

Wang et al., "Effects of betaine supplementation on rumen fermentation, lactation performance, feed digestibilities and plasma characteristics in dairy cows", "Journal of Agricultural Science", Jan. 1, 2010, pp. 487-495, vol. 148, Publisher: Cambridge University Press.

Peng et al., "Effects of Butyrate on Intestinal Barrier Function in a Caco-2 Cell Monolayer Model of Intestinal Barrier", "Pediatric Research", Jan. 1, 2006, vol. 61, No. 1, Publisher: International Pediatric Research Foundation, Inc.

Fernandez et al., "Effects of dairy products on intestinal integrity in heat-stressed pigs", "Temperature", Jan. 1, 2014, vol. 1, No. 2.

Dai et al., "Effects of dietary glutamine and gammaaminobutyric performance, carcass characteristics and serum parameters in broilers under circular heat stress", "Animal Feed Science and Technology", Jan. 1, 2011, pp. 51-60, vol. 168, Publisher: Elsevier.

Claus et al., "Effects of feeding fat-coated butyrate on mucosal morphology and function in the small intestine of the pig", "Journal of Animal Physiology and Animal Nutrition", Jan. 1, 2006, pp. 312-318, vol. 91, Publisher: The Authors.

Weber et al., "Effect of sodium butyrate on growth performance and response to lipopolysaccharide in weanling pigs", "J. Anim. Sci", Jan. 1, 2008, pp. 442-450, vol. 86, Publisher: ASAS.

Heugten et al., "Effects of organic forms of zinc on growth performance, tissue zinc distribution, and immune response of weanling pigs", "J. Anim. Sci.", Jan. 1, 2003, pp. 2063-2071, vol. 81, Publisher: American Society of Animal Science.

Fernandez et al., "Effects of supplemental zinc amino acid complex on gut integrity in heat-stressed growing pigs", "Animal", Jan. 1, 2013, Publisher: The Animal Consortium.

Lewis et al., "Enhanced Translocation of Bacteria Across Metabolically Stressed Epithelia is Reduced by Butyrate", "Butyrate and Epithelial Permeability", Jul. 1, 2010, vol. 16, No. 7, Publisher: Inflamm Bowel Dis.

Mercado et al., "Enhancement of Tight Junctional Barrier Function by Micronutrients: Compound-Specific Effects on Permeability and Claudin Composition", Nov. 1, 2013, vol. 8, No. 11, Publisher: PLOS.

Carlson et al., "Evaluation of various inclusion rates of organic zinc either as polysaccharide or proteinate complex on the growth performance, plasma, and excretion of nursery pigs", "J Anim. Sci.", Jan. 1, 2004, pp. 1359-1366, vol. 82, Publisher: American Society of Animal Science.

Borne et al., "Fat coating of Ca butyrate results in extended butyrate release in the gastrointestinal tract of broilers", "Livestock Science", Jan. 1, 2015, pp. 96-100, vol. 175, Publisher: Elsevier.

Guilloteau et al., "From the gut to the peripheral tissues: the multiple effects of butyrate", "Nutrition Research Reviews", Jan. 1, 2010, pp. 366-384, vol. 23, Publisher: The Authors.

Olubodun et al., "Glutamine and glutamic acid supplementation enhances performance of broiler chickens under the hot and humid tropical condition", "Italian Journal of Animal Science", Jan. 1, 2015, vol. 14, No. 3263, Publisher: IJAS.

Payne et al., "Growth and intestinal morphology of pigs from sows fed two zinc sources during gestation and lactation", "J. Anim. Sci", Jan. 1, 2006, pp. 2141-2149, vol. 84, Publisher: American Society of Animal Science.

Geiger et al., "Heat Shock Proteins Are Important Mediators of Skeletal Muscle Insulin Sensitivity", "Exerc Sport Sci Rev", Jan. 1, 2011, pp. 34-42, vol. 39, No. 1, Publisher: NIH Public Access.

Rogers et al., "Heat shock proteins: in vivo heat treatments reveal adipose tissue depot-specific effects", "J Appl Physiol", Jan. 1, 2015, pp. 98-106, vol. 118, Publisher: American Physiological Society.

Quinteiro et al., "Heat stress impairs performance parameters, induces intestinal injury, and decreases macrophage activity in broiler chickens", Jan. 1, 2010, Publisher: Poultry Science Association Inc.

Ju et al., "Heat stress upregulation of Toll-like receptors 2/4 and acute inflammatory cytokines in peripheral blood mononuclear cell (PBMC) of Bama miniature pigs: an in vivo and in vitro study", "Animal", Jan. 1, 2014, pp. 1-7, Publisher: The Animal Consortium.

Liu et al., "Heat stress induced damage to porcine small intestinal epithelium associated with downregulation of epithelial growth factor signaling", "Journal of Animal Science", Jan. 1, 2009, pp. 1941-1949, vol. 87.

(56) References Cited

OTHER PUBLICATIONS

Pearce et al., "Heat Stress reduces barrier function and alters intestinal metabolism in growing pigs", "J. Anim. Sci", Jan. 1, 2012, pp. 257-259, vol. 90, Publisher: ASAS.

Pearce et al., "Heat Stress Reduces INtestinal Barrier Integrity and Favors INtestinal Glucose Transport in Growing Pigs", Aug. 1, 2013, vol. 8, No. 8, Publisher: PLOS.

Pearce et al., "Heat stress and reduced plane of nutrition decreases intestinal integrity and function in pigs", "J Anim. Sci", Jan. 1, 2013, pp. 5183-5193, vol. 91, Publisher: American Society of Animal Science.

Gupte et al., "Heat Treatment Improves Glucose Tolerance and Prevents Skeletal Muscle Insulin Resistance in Rats Fed a High-Fat Diet", "Diabetes", Mar. 1, 2009, vol. 58.

Campos, "High ambient temperature alleviates the inflammatory response and growth depression in pigs challenged with *Escherichia coli* lipopolysaccharide", "The Veterinary Journal", Jan. 1, 2014, pp. 404-409, vol. 200, Publisher: Elsevier.

Chai et al., "High-dose dietary zinc oxide mitigates infection with transmissible gastroenteritis virus in piglets", "BMC Vet Re.", Jan. 1, 2014, vol. 10, No. 75, Publisher: BioMed Central.

Lalles et al., "Impact of bioactive substances on the gastrointestinal tract and performance of weaned piglets: a review", "Animal", Jan. 1, 2009, pp. 1625-1643, vol. 3, No. 12, Publisher: The Animal Consortium.

Sargeant et al., "Inflammatory response of porcine epithelial IPEC J2 cells to enterotoxigenic *E. coli* infection is modulated by zinc supplementation", "Molecular Immunology", Jan. 1, 2011, pp. 2113-2121, vol. 48, Publisher: Elsevier.

Hedemann et al., "Influence of dietary zinc and copper on digestive enzyme activity and intestinal morphology in weaned pigs", "J. Anim. Sci", Jan. 1, 2006, pp. 3310-3320, vol. 84, Publisher: American Society of Animal Science.

Bernabucci et al., "Metabolic and hormonal acclimation to heat stress in domesticated ruminants", "Animal", Jan. 1, 2010, pp. 1167-1183, vol. 4, No. 7, Publisher: The Animal Consortium.

Sargeant et al., "The metabolic impact of zinc oxide on porcine intestinal cells and enterotoxigenic *Escherichia coli* K88", "Livestock Science", Jan. 1, 2010, pp. 45-48, vol. 133, Publisher: Elsevier.

Zeisel et al., "Metabolic crosstalk between choline/1-carbon metabolism and energy homeostasis", "Clin Chem Lab Med", Jan. 1, 2013, pp. 467-475, vol. 51, No. 3.

Chang et al., "The microbial metabolite butyrate regulates intestinal macrophage function via histone deacetylase inhibition", Feb. 11, 2014, pp. 2247-2252, vol. 111, No. 6, Publisher: Cross Mark.

Ji et al., "Microbial metabolite butyrate facilitates M2 macrophage polarization and function", Jan. 1, 2016, Publisher: Scientific Reports.

Selkirk et al., "Mild endotoxemia, NF-!B translocation, and cytokine increase during exertional heat stress in trained and untrained individuals", "Am J Physiol Regul Integr Comp Physiol", Jan. 1, 2008, pp. R611-R623, vol. 295.

Rhoads et al., "Nutritional Interventions to Alleviate the Negative consequences of heat stress", Jan. 1, 2013, pp. 267-276, vol. 4, Publisher: American Society for Nutrition. Adv. Nutr.

Biagi et al., "Performance, intestinal microflora, and wall morphology of weanling pigs fed sodium butyrate", "J. Anim. Sci.", Jan. 1, 2007, p. 11841191, vol. 85, Publisher: American Society of Animal Science.

Canani et al., "Potential beneficial effects of butyrate in intestinal and extraintestinal diseases", "World Journal of Gastroenterology", Mar. 28, 2011, pp. 1519-1528, vol. 17, No. 12, Publisher: Baishideng.

Lim et al., "Pre-existing inflammatory state compromises heat tolerance in rats exposed to heat stress", "Regulatory, Integrative and Comparative Physiology", Jan. 1, 2007, pp. R186-R194, vol. 292, Publisher: American Journal of Physiology.

Gathiram et al., "Prevention of endotoxaemia by non-absorbable antibiotics in heat stress", Jan. 1, 1987, pp. 1364-1368, vol. 40, Publisher: J Clin Pathol.

Liu et al., "Reduction of intestinal mucosal immune function in heat-stressed rats and bacterial translocation", "Int. Hyperthermia", Jan. 1, 2012, Publisher: Informa Healthcare.

Valenzano et al., "Remodeling of Tight Junctions and Enhancement of Barrier INtegrity of the CACO-2 Intestinal Epithelial Cell Layer by Micronutrients", "Micronutrient Enhancement of GI Epithelial Tight Junctions", Jul. 30, 2015, pp. 1-22, Publisher: PLOS one.

Dubose, "Role of bacterial endotoxins of intestinal origin in rat heat stress mortality", , pp. 31-36.

Dubose, "Role of bacterial endotoxins of intestinal origin in rat heat stress mortality", "Journal of Applied Physiology", Jan. 1, 1983, pp. 31-36, Publisher: The American Physiological Society.

Schilderink et al., "The SCFA butyrate stimulates the epithelial production of retinoic acid via inhibition of epithelial HDAC", "Am J Physiol Gastrointest Liver Physiol", Jan. 1, 2016, p. G1138G1146, vol. 310, Publisher: American Physiological Society.

Pearce et al., "Short-term exposure to heat stress attenuates appetite and intestinal integrity in growing pigs", "Journal of Animal Science", Nov. 21, 2014, pp. 5444-5454, vol. 92, Publisher: ASAS.

Piva et al., "Sodium butyrate improves growth performance of weaned piglets during the first period after weaning", "ITAL.J. ANIM.SCI.", Jan. 28, 2002, pp. 35-41, vol. 1.

Lin et al., "Strategies for preventing heat stress in poultry", "Worlds Poultry Science Journal", Mar. 1, 2006, vol. 62, Publisher: Worlds Poultry Science Association.

Lambert, "Stress-induced gastrointestinal barrier dysfunction and its inflammatory effects", "Journal of Animal Science", Jan. 1, 2009, pp. E101-E108, vol. 87, Publisher: American Society of Animal Science.

Zhang et al., "Supplemental zinc reduced intestinal permeability by enhancing occludin and zonula occludens protein-1 (ZO-1) expression in weaning piglets", "British Journal of Nutrition", Jan. 1, 2009, pp. 687-693, vol. 102, Publisher: The Authors.

Crane et al., "Zinc protects against shiga-toxigenic *Escherichia coli* by acting on host tissues as well as on bacteria", "BMC Microbiology", Jan. 1, 2014, vol. 14, No. 145, Publisher: BioMed Central.

Wessels et al., "Zinc dyshomeostasis during polymicrobial sepsis in mice involves zinc transporter Zip14 and can be overcome by zinc supplementation", "Am J Physiol Gastrointest Liver Physiol", Aug. 13, 2013, p. G768G778, Publisher: American Physiological Society.

Scrimgeour et al., "Zinc and diarrheal disease: current status and future perspectives", "Wolters Kluwer Health", Jan. 1, 2008, pp. 711-717, vol. 11, Publisher: Lippincott Williams and Wilkins.

Hu et al., "Zinc oxide influences intestinal integrity the expressions of genes asociated with inflammation and TLR4-meyloid differentiation factor 88 signaling pathways in wenling pigs", "Innate Immunity", Jan. 1, 2013, Publisher: SAGE.

Hu et al., "Zinc OxideMontmorillonite Hybrid Influences Diarrhea, Intestinal Mucosal Integrity, and Digestive Enzyme Activity in Weaned Pigs", "Biol Trace Elem Res", Apr. 28, 2012, Publisher: Springer.

Queiroz et al., "Zinc treatment ameliorates diarrhea and intestinal inflammation in undernourished rats", "BMC Gastroenterology", Jan. 1, 2014, vol. 14, No. 136, Publisher: BioMed Central.

European Patent Office, "Extended European Search Report," issued in connection with European Patent Application No. 16818812.6-1106, dated Oct. 29, 2018, 9 pages.

Mani et al., "The protective effects of Butipearl Z during heat stress as measured through in vitro studies with swine intestinal epithelial cells and in vivo swine trial," Journal of Animal Science, vol. 94, Mar. 31, 2016, 1 page.

* cited by examiner

TREATMENT OF ENTERIC STRESS FROM HEAT AND INFECTION IN HUMANS AND ANIMALS BY SUPPLEMENTATION WITH ZINC AND BUTYRIC ACID

REFERENCE TO RELATED APPLICATIONS

This application claims priority to U.S. Patent Application Ser. No. 62/186,831, filed Jun. 30, 2015.

BACKGROUND OF THE INVENTION

The present invention relates generally to reducing the effect of stress in humans and animals and especially production animals and, more specifically, to the feeding of a combination of zinc and butyric acid for the treatment or amelioration of enteric stress from heat stress or disease stress.

High summer temperatures result in enormous amounts of physiological stress to production animals, leading to decreased feed intake, decreased growth rate and decreased feed conversion. During periods of rapid increasing temperature and humidity (expressed as a high humidity index (HI)), animals adjust to the increasing HI over a period of weeks. During this period, stress from HI to the animal causes the body core temperature to rise, resulting in an increase of the blood flow from the organs to the skin of the animal which allows for rapid cooling of the inner body core. Once the HI reaches a specific threshold, the animal is no longer able to effectively dissipate heat from the body core. This causes the animal's systemic blood flow to be diverted to the peripheral tissues to mitigate the heat stress, which leads to decreased blood flow to the intestine. These heat stressed animals are not in a position to consume any feed. The resulting decreased feed intake combined with lower blood flow to the intestine leads to villi damage, a decreased absorptive area for nutrients and sloughing of the intestinal epithelial cells. All of these combined effects result in a loss of intestinal integrity.

Swine encounter multiple pathogens throughout their life including viruses, bacteria, fungi and parasites. Any infection during the early life stages, particularly in nursery and early weaned piglets, can cause severe morbidity and mortality. It is difficult to predict the occurrence of any such event, and any disease outbreak results in severe economic losses. Therefore, it is important to develop strategies for these health challenges to decrease the mortality, maintain the growth of the animals and mitigate the losses. Most infections of agricultural animals occur through the gastrointestinal (GI) route. One example of such infection with huge economic potential is porcine epidemic diarrhea virus (PEDV). The PEDV coronavirus infects the enterocytes of the small intestine, resulting in severe inflammation of the gastrointestinal tract leading to diarrhea and decreased nutrient and water absorption. In suckling pigs, a severe PEDV infection commonly results in mortality. In newly weaned pigs, clinical signs lasts for approximately 7-14 days. Clinical signs include: decreased feed intake, decreased tissue accretion, and diarrhea; however, mortality is rarely observed. Because the animal's growth is affected significantly, they never regain their growth potential and it leads to huge economic losses to the producers.

The pathogenesis of any enteric disease is complex and involves different cellular pathways. These include inflammatory and immune signaling, oxidative stress, energy sensing, osmotic and microbial homeostasis pathways. Compounds which can counteract one or more of these pathways have the potential to mitigate the severity or prevent the negative effects of gastrointestinal infections. Additionally, compounds that augment intestinal restitution and recovery can reduce the impact that enteric pathogens may have on intestinal function and integrity, pig performance, wellbeing and may help the animals regain their growth potential.

Heat stress, infection with enteric viruses or bacteria will increase the permeability of the intestinal cells. This allows bacterial compounds such as lipopolysaccharide (LPS) and/or other noxious substances from the intestinal lumen to get through the intestinal barrier and cause an unwarranted inflammatory and immune response in animals. Compounds that improve or sustain intestinal integrity can decrease the effect of heat stress or disease challenges on intestinal integrity and can improve the growth of the animals during heat stress or infection.

SUMMARY OF THE INVENTION

The present invention includes the use of a salt of zinc and butyric acid, in a 1:2 ratio, (ZBA) which in a preferred embodiment is an encapsulated form of zinc and butyric acid salt (EZBA), to improve intestinal integrity and reduce the effects of heat stress, enteric disease challenges and other intestinal stress conditions in production animals. EZBA improves feed intake, feed conversion and weight gain during heat stress or enteric disease challenge. EZBA is fed between 50 ppm and 10,000 ppm, but most commonly between 300 and 2000 ppm. It has been discovered that feeding EZBA before or during heat stress and/or a disease challenge shortens the recovery period after a stress condition.

EZBA preferably is encapsulated to control the release of ZBA throughout the digestive system. An encapsulated form of EZBA preferably contains at least 20% ZBA to 60% ZBA, optimally at 35% to 45% ZBA. A method (co-pending U.S. patent application Ser. No. 15/198,775, filed Jun. 30, 2016, which claims priority to No. 62/186,787, filed Jun. 30, 2015, and which is incorporated herein in its entirety by this reference) has been developed to control the rate of release characteristics of the active ingredient, ZBA, by the use of excipients, such as salts, aqueous salts, aqueous organic salts, ionic surfactants, non-ionic surfactants, such as glycerol, polyethylene glycol derivatives, simple or complex sugar molecules such as glucose, dextran, and inulin, to modify hydrogenated vegetable oil used in the encapsulation process.

The present invention more particularly includes the encapsulation or coating of metal butyric acid salts, namely zinc, sodium, potassium, calcium, magnesium, iron, copper, chromium, manganese, or any other minerals in a modified fat matrix to create a spherical granule (approximately 0.1 to 2.0 mm in diameter and more optimally 0.5 to 1.2 mm in diameter). The granules have an internal three-dimensional (3D) structure consisting of channels originating from the interior of the granules and terminating at the granule surface which allows for a controlled and sustained release of the active ingredient through the dissolution of the porous structure. The active ingredient present in the granules may be at 1 to 70 wt %.

The present invention is further directed to the use of a group of compounds/reagents for controlling the release of feed additive, nutritional, and/or pharmaceutical ingredients from hydrogenated vegetable oil (HVO), including preferably hydrogenated palm oil (HPO), or other high melting fat or wax micro bead encapsulations generated with spray freeze technology or other similar technologies. Due to the chemical property of the active ingredients and unique characteristics of gut physiology for humans and other animals, targeted delivery and controlled release of the active ingredients is required for optimal efficacy. In poultry for example, the retention time of feed in the gut is relatively short and there is a need for rapid or faster release of the active ingredient to the gut from the encapsulation. In a bovine (ruminant), on the other hand, a slower release is required to allow for the targeted delivery of the active ingredient in the hindgut. In addition, due to the high acid level in the stomach, active ingredients may have to be protected from degradation to be released in the small intestine. Active ingredients have to be released at the right time and at the right location to be efficacious. There have been reports and practices of using HPO or high melting fat for encapsulation of active ingredients, but there have been no reports of methodologies to modify the characteristics of the fat matrix to control the release of actives with this encapsulation system. In the current invention propylene glycol, tween-20, polyethylene glycol, water, aqueous salt solutions, aqueous potassium hydroxide solution, and other polar compounds that are liquid under ambient temperatures and polar powder compounds, such as amino acids, salts and the like, that do not mix well with fat, were used at different concentrations to either increase or decrease the release of active ingredients from encapsulation. When these compounds were included one at a time or in combination, the release of active ingredients from the encapsulation beads was modified. The more modifiers included, the faster the release. The lower the amount of modifiers included, the slower the release. This was demonstrated with ZBA (the zinc salt of butyric acid in a molar ratio of 1:2) as the encapsulated active ingredient but would apply to other feed additives, nutritional and pharmaceutical active ingredients as well.

DETAILED DESCRIPTION OF THE PREFERRED EMBODIMENTS

The compounds of this invention may be administered to subjects (humans and animals, including companion animals, such as dogs, cats and horses) in need of such treatment in dosages that will provide optimal pharmaceutical efficacy. It will be appreciated that the dose required for use in any particular application will vary from subject to subject, not only with the particular compound or composition selected, but also with the route of administration, the nature of the condition being treated, the age and condition of the subject, concurrent medication or special diets then being followed by the subject, and other factors which those skilled in the art will recognize.

A suitable dosage level of EZBA of the present invention is about 50 to 10,000 ppm in animal feed. Preferably, the dosage range will be about 500 ppm to 5000 ppm. Compositions of the present invention may be provided in a formulation comprising about 25 ppm to 5000 ppm of the active ingredient (ZB A).

The EZBA in a preferred embodiment is a combination of zinc oxide and butyric acid, although other compounds of zinc, particularly mineral and organic salts of zinc may be used. Preferably, the EZBA is between about 10% and 90% of zinc and between about 90% and about 10% of butyric acid.

"Efficacious amount" for the purposes of this application is defined to be the amount of a compound or composition or derivatives thereof of the present invention is an amount that, when administered to a subject, will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of the impairment, and the therapeutics or combination of therapeutics selected for administration, and the mode of administration. The skilled worker can readily determine the effective amount for a given situation by routine experimentation.

In preferred embodiments of the present invention, the effective amount of a salt of zinc and butyric acid ranges between 50 ppm and 10,000 ppm of the product being treated and all values between such limits, including, for example, without limitation or exception, 61 ppm, 237 ppm 1,011 ppm, 2,170 ppm, 6,573 ppm and 9999 ppm. Stated another way, in preferred embodiments of the invention, the dosage can take any value "abcde" ppm wherein a is selected from the numerals 0 and 1, and b, c, d and e are each individually selected from the numerals 0, 1, 2, 3, 4, 5, 6, 7, 8 and 9, with the exception that d cannot be less than 5 if a, b, c and d are all 0.

Example 1

Cell Culture Work

Materials and Methods

Figure 1:
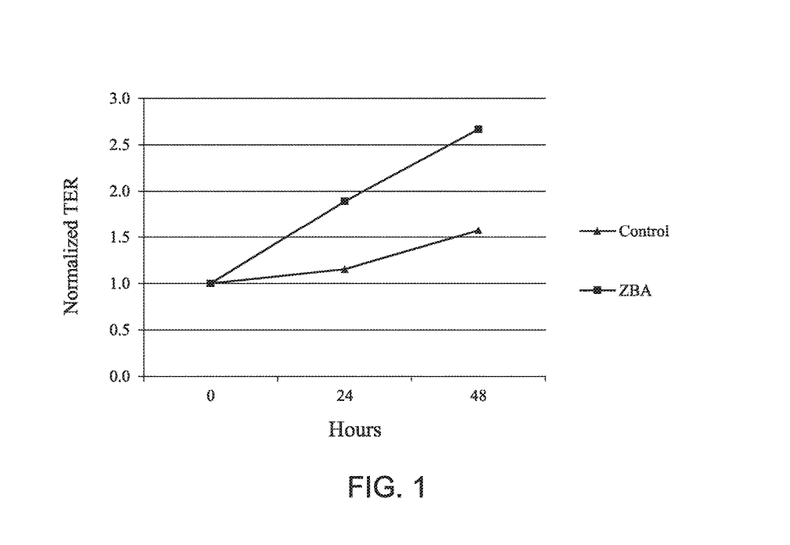
FIG. 1 is a chart of the effect of 1 mM ZBA on the transepithelial resistance (TER) of cultured pig ileal intestinal cells (IPEC-J2 cells) under normal conditions; the Control treatment has no added zinc.

The data in FIG. 1 and corresponding table (Table 1) show that growing IPEC-J2 epithelial cells in the presence of ZBA causes them to have increased trans-epithelial resistance. This indicates that the tight junctions between the cells are well formed when compared to the alternate treatments and demonstrates improved intestinal integrity.

TABLE 1

Effect of heat stress challenge on IPEC-J2 cells under various treatments

| Treatment | 0 h | 12 h | 24 h | 36 h | 48 h |
|---|---|---|---|---|---|
| Control-TN | 1.00 | 1.97 | 2.11 | 2.52 | 2.81 |
| Control-HS | 1.00 | 1.47 | 1.81 | 2.10 | 2.24 |
| Zinc Sulfate-HS | 1.00 | 1.67 | 1.89 | 2.19 | 2.31 |
| ZBA-HS | 1.00 | 2.04 | 2.24 | 2.60 | 2.76 |
| Calcium Butyric Acid Salt-HS | 1.00 | 1.58 | 1.74 | 1.96 | 2.10 |

TN—Thermoneutral
HS; Heat stress

Figure 2:
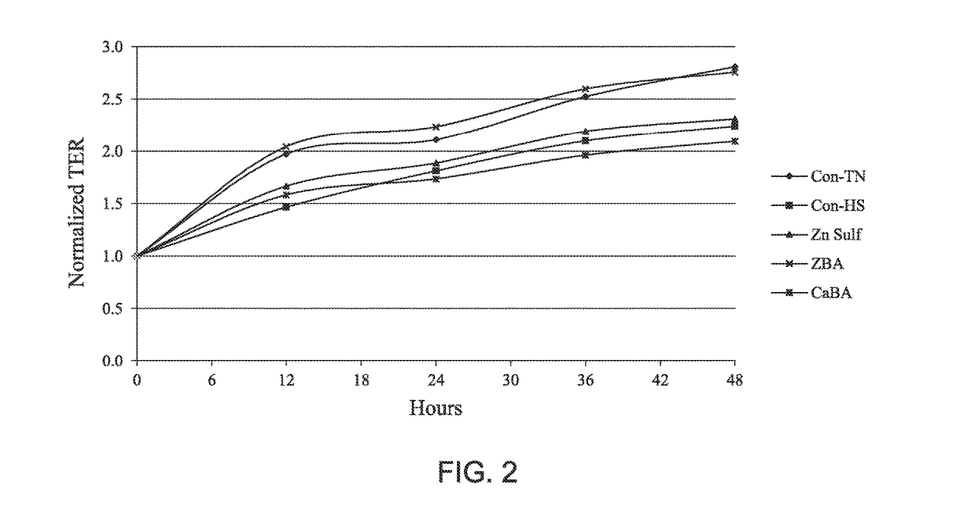
FIG. 2 is a chart of the effect of 300 µM concentration of different test compounds on the transepithelial resistance (TER) values of IPEC-J2 cells under heat stress conditions.

When animals undergo heat stress, the increased temperature leads to damage of the epithelial layer as well as withdrawal of tight junction proteins to the cytoplasm of the epithelial cells, thus compromising the tight junctions. The compromised tight junctions allow for toxins and other inflammatory substances to enter the systemic circulation. Compared to growing the cells under thermoneutral conditions (FIG. 1), ZBA also improves the trans-epithelial resistance when cells are grown under heat stress. As reported in FIG. 2, cells were treated with the test compounds and incubated at 41.5° C. (Con-TN) Control-Thermoneutral conditions—37° C. (CON—HS)—Control-Heat Stress conditions—41.5° C. (Zn Sulf) 300 µM Zinc Sulfate under Heat Stress Conditions—41.5° C. (ZBA) 300 µM ZBA under Heat Stress Conditions—41.5° C. (CaBA) 300 µM Calcium and Butyric Acid Salt under Heat Stress Conditions—41.5° C. The presence of 300 µM ZBA in the cell culture media improves the trans-epithelial resistance to the level of cells grown that are grown at thermoneutral conditions at 37° C., which is the normal temperature at which the cells are grown. The treatments of zinc or butyric acid separately, as zinc sulfate or calcium and butyric acid salt, do not improve the trans-epithelial resistance as compared to the un-treated heat stress cells (FIG. 2).

Example 2

Heat Stress Trial in Swine

To determine the effect of feeding EZBA on intestinal integrity during metabolic and physiological stress, an animal trial was performed which uses pigs as the experimental model and heat stress for the stress model. The effect of the EZBA was determined by comparing the growth of the pigs treated with EZBA to the growth of the untreated pigs.

During the acclimation phase, which comes before the heat stress period, twenty four grower pigs weighing approximately 30 kg were used for the study (n=12/trt) in a randomized complete block design. The pigs were fed two treatments, a control treatment with no ZBA added and an encapsulated ZBA treatment. The EZBA treatment contained 3000 ppm of ZBA, fed in an encapsulated form of 40% ZBA and 57.5% hydrogenated palm oil and 2.5% propylene glycol. The pigs were blocked by weight and feed and water were provided ad libitum. Pigs were on the respective treatments for 28 days at ambient temperature to allow for enrichment of the test compounds. The pigs were weighed and blood samples were collected every week.

After the collection, the animals were subjected to a bi-phasic heat stress to simulate the natural heat stress model, where during the day time the temperature was around 33° C. and during the night it was around 22° C., for 7 days. Blood was collected every twelve hours. Rectal temperature of each pig was measured every two hours. At the end of this period six pigs from each group were euthanized and Using chamber studies were performed on fresh ileum and colon from each pig. Trans-epithelial resistance and macromolecule transport using FITC labeled dextran were determined to measure the effect of supplementation of the different zinc compounds on intestinal integrity and health during heat stress.

Figure 3A:
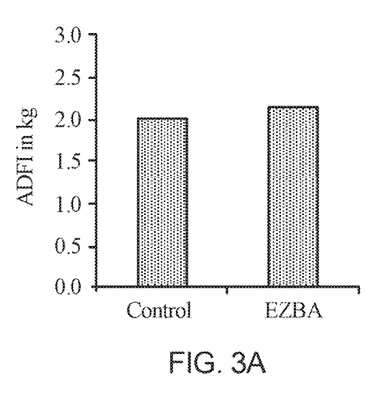
FIG. 3A is a chart of the average daily feed intake (ADFI) for the control and EZBA fed pigs during the pre-heat stress period of the trial.
Figure 3B:
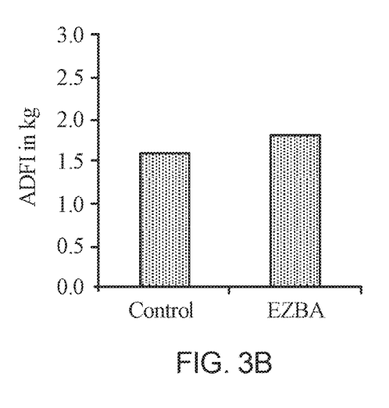
FIG. 3B is a chart of the average daily feed intake (ADFI) for the control and EZBA fed pigs during the heat stress period of the trial.

During both the acclimation phase and the heat stress period, the EZBA fed pigs had a higher feed intake as compared to the control pigs (FIG. 3B).

Figure 4A:
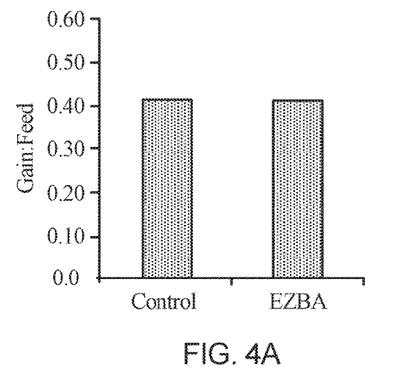
FIG. 4A is a chart of the Gain:Feed for the control and EZBA fed pigs during the pre-heat stress period of the trial.
Figure 4B:
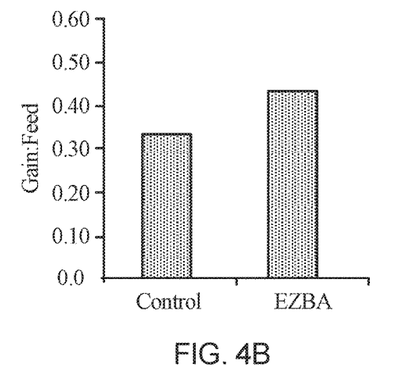
FIG. 4B is a chart of the Gain:Feed for the control and EZBA fed pigs during the heat stress period of the trial.
Figure 5A:
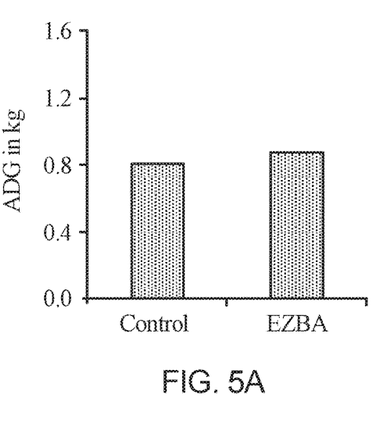
FIG. 5A is a chart of the Average Daily Gain (ADG) for the control and EZBA fed pigs during the pre-heat stress period of the trial.
Figure 5B:
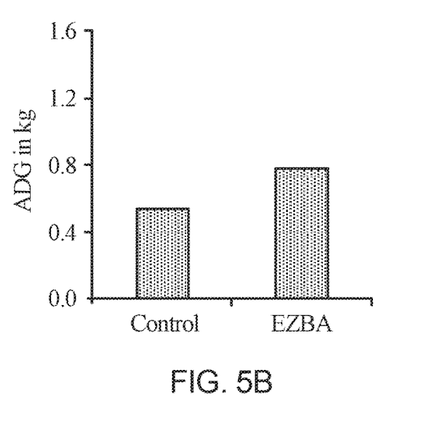
FIG. 5B is a chart of the Average Daily Gain (ADG) for the control and EZBA fed pigs during the heat stress period of the trial.

During the acclimation phase, the control and EZBA treated pigs had similar Gain:Feed (FIG. 4A) and average daily gain (FIG. 5A), but during the heat stress period, the EZBA fed pigs had a higher Gain:Feed (FIG. 4B) and average daily gain (FIG. 5B) as compared to the control fed pigs.

Figure 6:
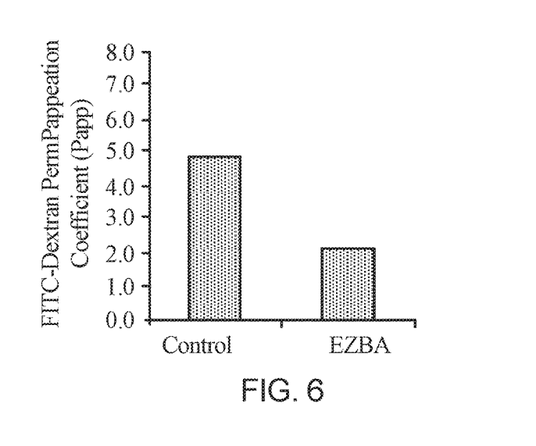
FIG. 6 is a chart of the intestinal integrity (Papp) measured by FITC-Dextran permeability of the ileum intestinal samples for the control and EZBA fed pigs at the end of the heat stress period.

Macromolecule transport through the intestinal tissue, as measured by FITC-Dextran transport, was lower with the EZBA treated group, as compared to the control group during heat stress (FIG. 6). This indicates that the intestines of the EZBA fed pigs have more intact tight junctions than the intestines of the control fed pigs.

The results of the swine trial show that feeding EZBA can help alleviate the loss in feed intake that occurs during the stress period. In addition, feeding EZBA can help increase both the Gain:Feed ratio and weight gain when animals are being stressed, such as being exposed to excessive heat or any pathogenic challenges.

Example 3

Effectiveness of EZBA on Swine Infected with PEDV

Materials and Methods

Feed

Three nursery pig diets were manufactured at the Iowa State University Swine Nutrition Farm. All pigs were on a common corn-soybean meal basal diet that met or exceeded the NRC 2012 nutrient requirements for this size pig (Table 2). EZBA was included in the feed at 5 grams per kg feed and hand mixed into the feed, this supplied 550 ppm of supplemental zinc to the diet.

Animals, Housing, and Inoculation

A total of 32 mixed sex pigs were obtained from an Iowa State University source and delivered after weaning at an average initial body weight (BW) of 7.5±1.2 kg. Pigs were allotted based on sex and arrival BW across 2 treatments (Control and EZBA) with 16 pigs per treatment and 2 pigs per pen (8 pens per treatment).

There were 2 rooms in which these pigs were housed and both rooms contained equal numbers of pigs of each treatment. Pigs were provided the treatment diets for the duration of the study. They were allowed a 7 or 8 day adaptation to the diet and housing in which time, pre-challenge growth performance data were collected. During this first week a starter pellet diet was included at a 1:1 ratio with the treatment diet to ensure that the pigs started well prior to challenge. All pigs were equally split into two replications to allow for necropsies to be offset by 1 day. Therefore, the pre-challenge period was 7 days for replicate 1 and 8 days for replicate 2. Data were pooled for each replicate and was included in the model as a covariate if it significantly contributed to the model. Pigs were gastrically gavaged with 5 ml of $10^3$ $TC/D_{50}$ of the PEDV plaque-cloned isolate from Iowa (18984/2013) on 0 days post innoculation (DPI).

Growth Performance Calculations, Tissue Collection, and Analyses of Intestinal Sections Pigs and feeders were weighed at dpi −7/−8, 0, 5, 10, 15, and 20 to calculate average daily gain (ADG), average daily feed intake (ADFI), and gain to feed ratio (G:F). There were 2 pigs per pen for data including and prior to 5 dpi and 1 pig per pen for data including and after 10 days post infection (dpi). Upon arrival, pigs were confirmed PEDV naïve by fecal swab qPCR. To characterize the pathogenesis of PEDV, at dpi 0, 5, 10, 15 and 20 fecal swabs from all pigs and blood (~10 mL) from 1 pig per pen was obtained. The same pig was bled at each time point. All fecal swabs were analyzed for PEDV by qPCR.

At dpi 5 and 20, 8 pigs per treatment (1 pig per pen) were weighed, euthanized, and necropsied. Pigs were restrained and euthanized by intravenous administration of a lethal dose of sodium pentobarbital followed by exsanguination. Jejunum and ileum were collected, flushed with phosphate buffered saline, and formalin fixed. After 24 hours, fixed samples were removed from formalin and placed in ethanol. Tissues were paraffin embedded and sectioned for analysis.

TABLE 2

Ingredient composition of for the basal diets

|  | Control | EZBA |
|---|---|---|
| Ingredient, % | | |
| Corn | 50.76 | 50.26 |
| Soybean Meal | 19.00 | 19.00 |
| Soybean oil | 1.73 | 1.73 |
| Fishmeal, menhaden | 4.50 | 4.50 |
| Limestone | 0.35 | 0.35 |
| Whey, dried | 20.00 | 20.00 |
| Meat and Bone Meal | 2.04 | 2.04 |
| L-Lysine HCL | 0.43 | 0.43 |
| DL-Methionine | 0.16 | 0.16 |
| L-Threonine | 0.13 | 0.13 |
| L-Tryptophan | 0.03 | 0.03 |
| L-Valine | 0.07 | 0.07 |
| EZBA | — | 0.5 |
| Salt | 0.40 | 0.40 |
| SNF Grow-Fin Vit Premix | 0.25 | 0.25 |
| SNF Trace Mineral Premix | 0.15 | 0.15 |
| Calculated Composition | | |
| ME, kcal/kg | 3,408 | 3,408 |
| SID Lysine, % | 1.35 | 1.35 |
| STTD Phos., % | 0.40 | 0.40 |

Formalin-fixed, paraffin-embedded intestinal tissue sections were mounted on positively charged glass slides and oven-dried for 20 min at 60° C. Deparaffinization occurred with three changes of xylene for 5 min each followed by rehydration with 100% alcohol, 95% alcohol, 70% alcohol, tap water, and distilled water. Slides were then placed in 3% hydrogen peroxide (Fisher Scientific, Pittsburgh, Pa.), diluted in methanol, for 10 min followed by three changes of distilled water. Antigen retrieval was accomplished with 0.05% protease XIV (Sigma-Aldrichl, St. Louis, Mo.) for 2 min followed by three distilled water rinses. Approximately 200 ml of murine monoclonal 6C8 primary antibody specific for the nucleoprotein of PEDV (BioNote, Seoul, Korea), diluted 1:100, was applied to each slide, then transferred to a 37° C. incubator for 1 h, removed, uncovered, and rinsed with Tris Buffer Saline (TBS) (Fisher Scientific, Pittsburgh, Pa.) for 3 min. LSAB2-HRP Link and Label (Dako, Carpinteria, Calif.) were then applied to each slide for 10 mi and rinsed in TBS for 3 min, respectively. DAB substrate chromogen (Dako, Carpinteria, Calif.) was applied to the slides for 5 min followed by a distilled water rinse for 3 min. The slides were then counterstained in hematoxylin, dehydrated, cleared with Pro-Par clearant (Anatech LTD, Battel Creek, Mich.), and cover-slipped. Immunohistochemistry (IHC) slides were prepared for all five small intestine sections of all challenged pigs. Antigen detection was semi-quantitatively scored based on the following criteria: 0=no signal, 1=1-10% of villous enterocytes within the section showing a positive signal, 2=11-50% of villous enterocytes showing a positive signal, and 3=greater than 50% of villous enterocytes showing a positive signal. Semi-quantitative scores were recorded by a single blinded veterinary pathologist (Madson, D. M., Magstadt, D. R., Arruda, P. H., Hoang, H., Sun, D., Bower, L. P., Bhandari, M., Burrough, E. R., Gauger, P. C., Pillatzki, A. E., Stevenson, G. W., Wilberts, B. L., Brodie, J., Harmon, K. M., Wang, C., Main, R. G., Zhang, J., and Yoon, K. J., (2014). Pathogenesis of porcine epidemic diarrhea virus isolate (US/Iowa/18984/2013) in 3-week-old weaned pigs. Vet Microbiol. 174: 60-8).

The ISH protocol uses an oligonucleotide probe targeting the N gene of PEDV (5'-TGTTGCCATTACCACGACTC-CTGC-3') obtained from a commercial vendor (Invitrogen Custom Oligos, Life Technologies, Carlsbad, Calif.) with a 5' fluorescein label. The probe is reconstituted in a commercial hybridization buffer (Bond™ Hybridization Solution, Leica Biosystems, Newcastle Upon Tyne, UK) at 5 ng/µl and the procedure is performed using a commercially available system (Leica Bond-III, Leica Biosystems, Melbourne, Australia). Tissue sections are dewaxed using a commercial dewaxing solution and then treated with a commercially available enzymatic pretreatment (Bond™ Enzyme Pretreatment Kit, Leica Biosystems, Newcastle Upon Tyne, UK) for 5 min followed by 5 rinses with a commercial wash solution (Bond™ Wash Solution, Leica Biosystems, Newcastle Upon Tyne, UK). The diluted probe is applied and allowed to hybridize at 45° C. for 12 hours and then rinsed prior to incubation with an anti-FITC antibody for 30 minutes followed by application of a commercial chromagen system (Bond DAB Refine Kit, Leica Biosystems, Newcastle Upon Tyne, UK).

Intestinal sections were also stained to detect Ki67, a marker for stem cell proliferation. The monoclonal Ki67 antibody was purchased from Dako (Glostrup, Denmark) and has been previously published for pigs (Jung, Kwonil, Annamalai, Thavamathi, Lu, Zhongyan, and Saif, Linda J., (2015). Comparative pathogenesis of US porcine epidemic diarrhea virus (PEDV) strain PC21A in conventional 9-day-old nursing piglets vs. 26-day-old weaned pigs. Veterinary Microbiology. 178: 31-40). Ki67 was quantified by counting positive nuclei in 3 intact crypts that were orientated properly and had approximate average depth for that specific section.

Lesion scores were given for sections of ileum and jejunum that were routinely stained with H&E. Scores were given from 0 to 3, where 0=normal villus:crypt ratio (>4:1), 1=mild villus blunting (4:1-3:1) with rare fusion, 2=moderate villus blunting (3:1-2:1) and moderate fusion with lymphoid infiltration, and 3=severe villus blunting (<2:1) with severe fusion and lymphoid infiltration. The same person recorded lesion scores for all sections to eliminate scorer biases. Sections, staining, and scoring was done at the ISU Veterinary Diagnostic Lab using internal standards and protocols.

Data Analysis

Growth performance data were analyzed to determine effect of treatment, dpi, and treatment by dpi interaction and this model included the fixed effects of treatment, dpi, and treatment by dpi interaction. Start BW was used as a covariate for BW, ADG, and G:F estimates and replicate was used as a covariate for ADG estimates. Growth performance data were also analyzed over the entire 20 dpi period. The model included treatment as the fixed effect and start BW was used as a covariate for BW gain estimates. For all growth performance data, the repeated statement was used with a pen as the subject over time and the structure used was compound symmetry.

Results

Quantitative PCR for PEDV

Figure 7:
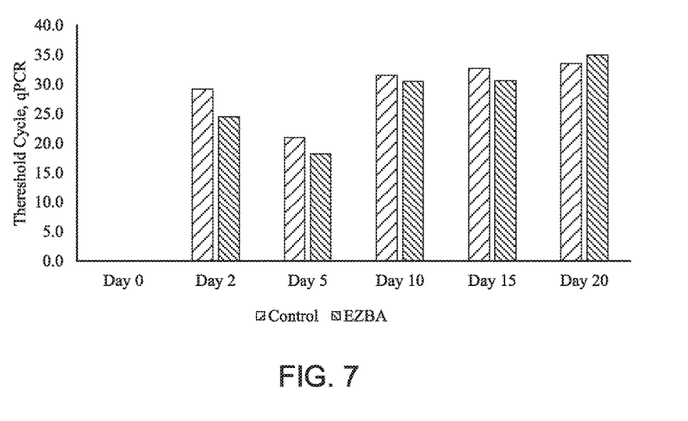
FIG. 7 is a chart of viral shedding of Porcine Epidemic Diarrhea Virus (PEDV) determined by qPCR on fecal swabs from pigs inoculated with porcine epidemic diarrhea virus (PEDV) and supplemented with EZBA in feed over 20 days post inoculation (DPI).

All pigs were positive for PEDV at least once during the study (FIG. 7). There was an effect of dpi where the lowest cycle threshold (Ct) value was at 5 dpi and increased thereafter for both PEDV treatments. PEDV values were not different between the two treatments.

Growth Performance

Figure 8A:
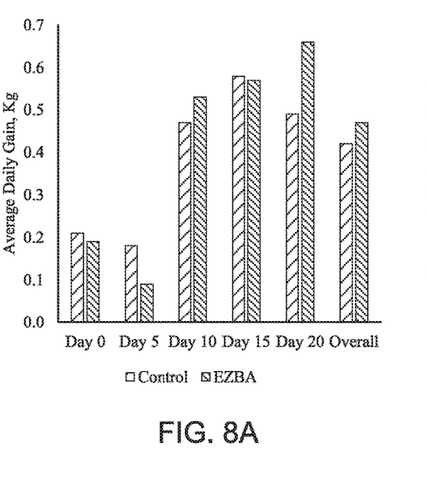
FIG. 8A is a chart of the average daily gain and FIG. 8B is a chart of the average daily feed intake of pigs inoculated with porcine epidemic diarrhea virus (PEDV) and supplemented with EZBA in feed over 20 days post inoculation (DPI).
Figure 8B:
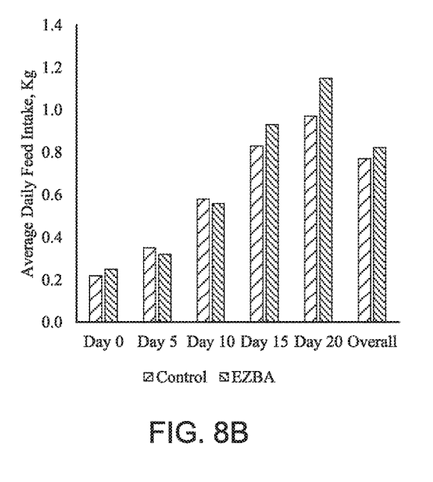

The EZBA treatment had a higher ADG at day 20 and also during the overall period whereas ADFI was higher on days 15 and 20 as well as during the overall period (FIGS. 8A and 8B).

Figure 9A:
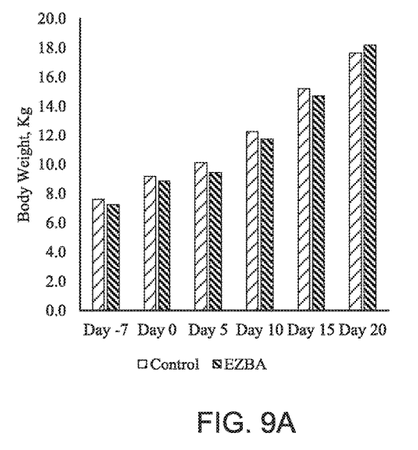
FIG. 9A is a chart of body weight and FIG. 9B is a chart of Gain: Feed of pigs inoculated with porcine epidemic diarrhea virus (PEDV) and supplemented with EZBA in feed over 20 days post inoculation (DPI).
Figure 9B:
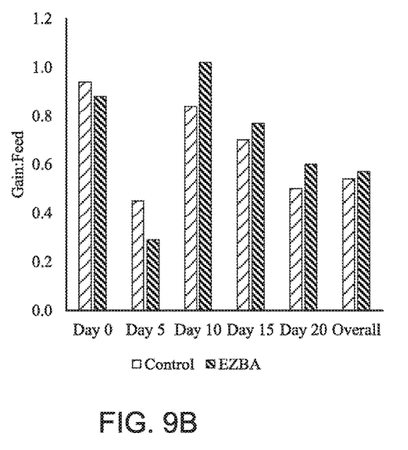

At day 20 the EZBA group had a higher body weight than the control group. Except for day 0 and day 5, Gain: Feed of EZBA group was higher than the control group throughout the experimental period (FIGS. 9A and 9B).

Figure 10A:
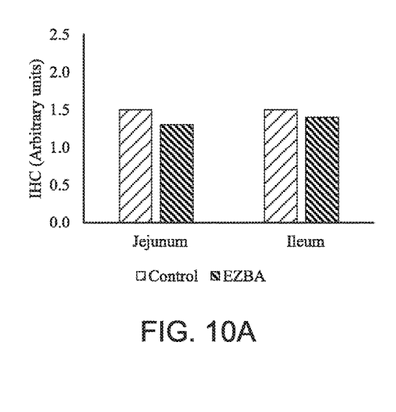
FIG. 10A is a chart of PEDV immunohistochemistry (IHC) and FIG. 10B is a chart of In situ hybridization (ISH) at 5 dpi of jejunum and ileum of pigs inoculated with porcine epidemic diarrhea virus (PEDV) and supplemented with EZBA in feed over 20 days post inoculation (DPI).
Figure 10B:
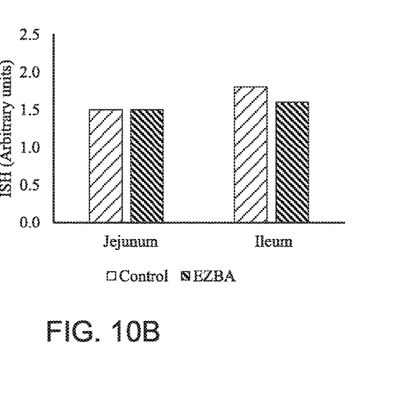

Immunohistochemistry for PEDV and Ki65, In Situ Hybridization for PEDV, and Lesion Scores Antigen and nucleic acid staining of PEDV was only observed at 5 dpi for PEDV treatments, as expected. There was no difference in jejunum or ileum PEDV IHC scores between the treatments. In both tissues PEDV IHC was lower in EZBA group and the ileum PEDV ISH scores for the EZBA treatment was lower than those of the control treatment. There was no PEDV IHC or ISH detected at 20 dpi (FIGS. 10A and 10B).

Figure 11A:
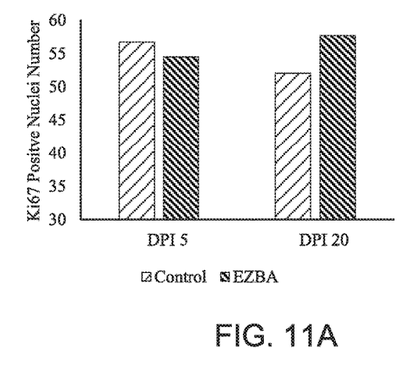
FIG. 11A is a chart of the jejunum and FIG. 11B is a chart of the ileum Ki67 immunohistochemistry of pigs inoculated with porcine epidemic diarrhea virus (PEDV) and supplemented with EZBA in feed over 20 days post inoculation (DPI).
Figure 11B:
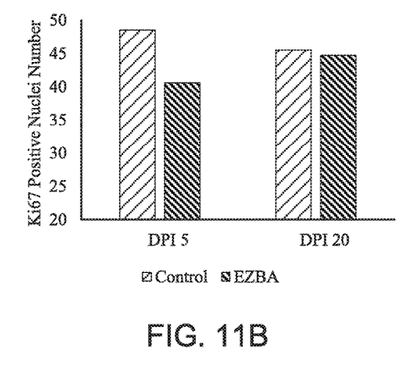

The positive nuclei counts of the control group at dpi 20 were lower in both the jejunum and ileum compared to dpi 5. In both the jejunum and ileum, EZBA pigs had greater Ki67 positive nuclei at 20 dpi compared with 5 dpi. This demonstrates that the EZBA treatment was able to increase the number of Ki67 positive nuclei and sustain the increase at 20 dpi compared with the Control. In the jejunum, the EZBA group had a significantly higher positive nuclei count compared to the control at dpi 20 (FIGS. 11A and 11B).

Figure 12A:
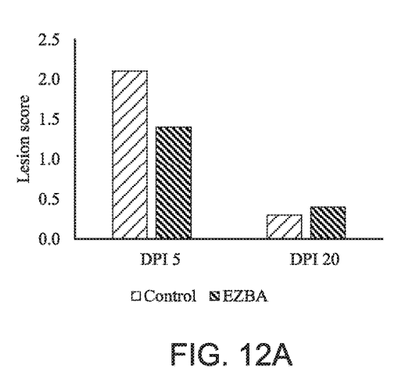
FIG. 12A is a chart of lesion score of the jejunum and FIG. 12B is a chart of lesions score of the ileum from pigs inoculated with porcine epidemic diarrhea virus (PEDV) and supplemented with EZBA in feed over 20 days post inoculation (DPI).
Figure 12B:
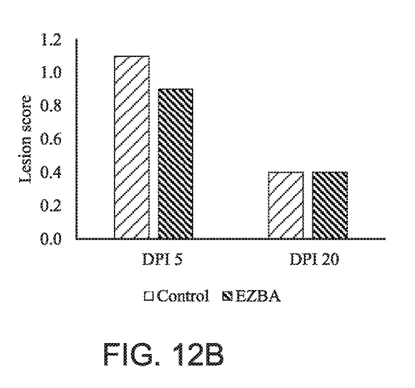

There was no treatment by dpi interaction or treatment effect of lesion score in both jejunum and ileum. There was a dpi effect in jejunum and ileum for lesion scores where there was a decrease in lesion scores at 20 dpi compared with 5 dpi regardless of treatment. EZBA significantly reduced the lesion score in the jejunum at dpi 5, and EZBA also reduced the lesion scores in the ileum compared to the control at dpi 5 (FIGS. 12A and 12B).

Morphology of Jejunum and Ileum

Figure 13A:
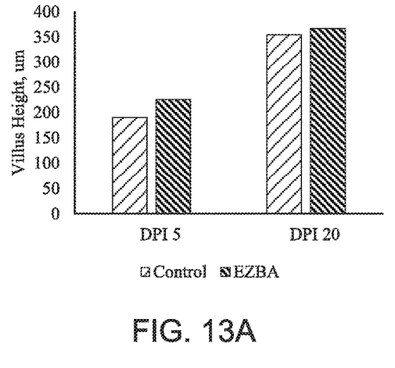
FIG. 13A is a chart of the villus height of the jejunum and FIG. 13B is a chart of the villus height of the ileum from pigs inoculated with porcine epidemic diarrhea virus (PEDV) and supplemented with EZBA in feed over 20 days post inoculation (DPI).
Figure 13B:
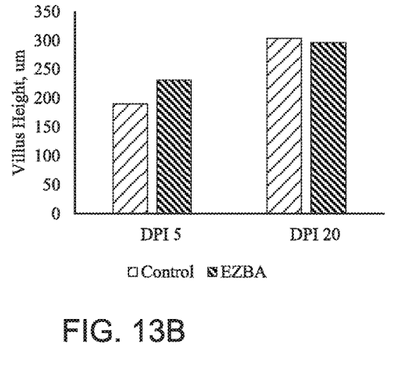

There was a treatment by dpi interaction for villi height in the jejunum and ileum. Regardless of treatment, jejunum and ileum villi height were increased at 20 dpi compared with 5 dpi. Villi height was numerically higher in the EZBA treatment at dpi 5 in both jejunum and ileum (FIGS. 13A and 13 B).

Figure 14A:
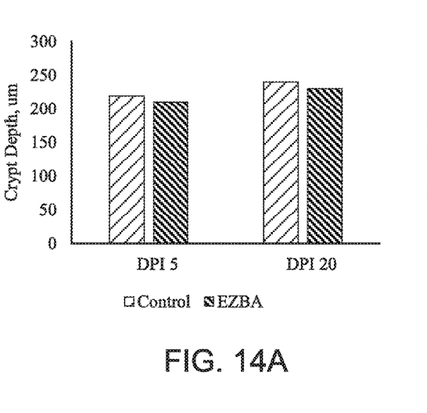
FIG. 14A is a chart of the crypt depth of the jejunum and FIG. 14B is a chart of the crypt depth of the ileum from pigs inoculated with porcine epidemic diarrhea virus (PEDV) and supplemented with EZBA in feed over 20 days post inoculation (DPI).
Figure 14B:
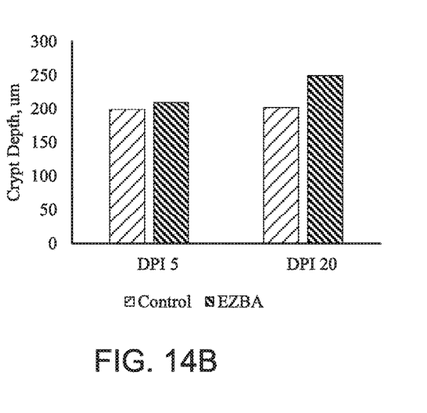

Crypt depth was not different in the jejunum on both days and in the ileum on dpi5. On dpi 20 crypt depth of the EZBA group in ileum was significantly higher than the control group (FIGS. 14A and 14 B).

Discussion

PEDV has significant negative impact on the health and growth of pigs. In this trial EZBA was studied to understand whether it could give protection and alleviate the negative effects during a PEDV infection in nursery pigs. Pigs were confirmed positive for PEDV 5 dpi using qPCR. ADG, ADFI, body weight were comparatively lower during the first ten days of infection in both treatment groups but the EZBA pigs recovered quickly and by d20 they had a better ADG, ADFI and body weight compared to the control pigs. G: F of EZBA pigs was also numerically higher from d10 onwards. Even though growth performance is not the focus of this study, these results present clear evidence that EZBA could help the ADFI in pigs which would improve the health as well as maintain the growth during viral infection.

IHC and ISH were performed to confirm and quantify the presence of PEDV protein and DNA in the jejunum and ileum. The EZBA group of pigs had a lower IHC values in the jejunum indicating the lesser presence of PEDV antigen and lower ISH values in both ileum and jejunum indicating lesser presence of PEDV genetic material. These results indicate that EZBA has the potential to decrease the proliferation of the virus which would result in decreased pathogenicity of the virus and help the animal recover quickly.

EZBA significantly reduced the lesion score in jejunum and also reduced the lesion score in ileum at dpi 5. Decreased lesion scores indicate that the intestinal tissues from EZBA pigs were better protected against PEDV compared to the control group. Ki67 is a stem cell marker which specifically binds to proliferating stem cells. Higher binding of Ki67 is an indication that the tissue is regenerating faster. In the jejunum, there was no difference between the Ki67 positive nuclei at dpi 5 but at dpi 20 EZBA pigs had a significantly higher amount of positive nuclei. Also, the positive nuclei value of the control group in both tissues decreased compared to dpi 5 where as the EZBA group increased. This indicates that EZBA group has the potential to stimulate the tissue regeneration faster after the PEDV infection. Severity of any infection can be contained by replacing the inflamed and infected tissues faster. Both zinc and butyric acid, ingredients of EZBA, have the potential to act on different cellular pathways to improve the recovery and increase the cell number of the GI tract under various inflammatory conditions which is evident from these results.

Jejunum and ileum morphology results also supported the beneficial effects of supplementing EZBA in nursery pig diets. Villus height and crypt depth were increased during the peak infection period, 5 dpi. This indicates that EZBA was able to blunt the severity of PEDV infection.

All this evidence strongly suggests that EZBA can maintain the gut health and barrier integrity and has the potential to alleviate the negative effects during PEDV infection.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A method of improving intestinal integrity and reducing the effects of heat stress, enteric disease challenges and other intestinal stress conditions in a human or an animal, comprising feeding the human or the animal an efficacious amount of an encapsulated salt of zinc and butyric acid (EZBA), wherein the EZBA contains between about 20% to about 60% zinc and butyric acid salt; said EZBA being encapsulated in a granule having an internal three-dimensional framework of channels to control the rate of release of EZBA from the granule; and wherein said granule, the EZBA being encapsulated in a mixture of vegetable oil and at least one modifier being a polar compound that is liquid at ambient temperature.

2. A method of improving feed intake, feed conversion and weight gain during heat stress or enteric disease challenge in a human or an animal, comprising feeding the human or the animal an efficacious amount of an encapsulated salt of zinc and butyric acid (EZBA); said EZBA being encapsulated in a granule having an internal three-dimensional framework of channels to control the rate of release of EZBA from the granule; and wherein said granule, the EZBA being encapsulated in a mixture of vegetable oil and at least one modifier being a polar compound that is liquid at ambient temperature.

3. The method of either claim 1 or claim 2, wherein said EZBA is fed between 50 ppm and 10,000 ppm.

4. The method of claim 2, wherein said EZBA contains between about 35% to about 45% zinc and butyric acid salt.

5. The method of claim 4, wherein the modifier is selected from the group consisting of salts, ionic surfactants, non-ionic surfactants, simple or complex sugar molecules and inulin.

6. The method of shortening the recovery period after a heat stress and/or disease challenge comprising feeding to an animal or a human in need thereof an efficacious amount of an encapsulated salt of zinc and butyric acid (EZBA) before or during the heat stress and/or disease challenge; said EZBA being encapsulated in a granule having an internal three-dimensional framework of channels to control the rate of release of EZBA from the granule; and wherein said granule, the EZBA being encapsulated in a mixture of vegetable oil and at least one modifier being a polar compound that is liquid at ambient temperature.

7. The method of claim 1, wherein said animal is selected from the group consisting of swine, poultry and horses.

8. The method of claim 1, wherein said EZBA is fed between 300 and 3000 ppm.

9. The method of claim 2, wherein said EZBA is fed between 300 and 3000 ppm.

10. The method of claim 6, wherein said EZBA is fed between 50 ppm and 10,000 ppm.

11. The method of claim 6, wherein said EZBA is fed between 300 and 3000 ppm.

12. The method of claim 6, wherein the non-ionic surfactants are at least one selected from the group consisting of glycerol and polyethylene glycol derivatives.

13. The method of claim 6, wherein the complex sugar molecules are at least one selected from the group consisting of glucose, dextran, and inulin.

14. The method of claim 1 whereby the EZBA comprises salt of zinc and butyric acid in a 1:2 ratio.

15. The method of claim 2 whereby the EZBA comprises salt of zinc and butyric acid in a 1:2 ratio.

16. The method of claim 6 whereby the EZBA comprises salt of zinc and butyric acid in a 1:2 ratio.

17. A method of improving intestinal integrity and reducing the effects of heat stress, enteric disease challenges and other intestinal stress conditions in a human and an animal, comprising feeding the human or the animal an efficacious amount of an encapsulated salt of zinc and butyric acid (EZBA); said EZBA being encapsulated in a granule having an internal three-dimensional framework of channels to control the rate of release of the EZBA from the granule; and wherein said granule, the EZBA being encapsulated in a mixture of vegetable oil and at least one modifier being a polar compound that is liquid at ambient temperature, wherein the at least one modifier is selected from the group consisting of glycerol and polyethylene glycol derivatives.

* * * * *